United States Patent
Rey

(10) Patent No.: US 8,494,620 B2
(45) Date of Patent: Jul. 23, 2013

(54) ELECTROCARDIOGRAPH FOR MAGNETIC RESONANCE IMAGING AND ELECTRODE PATCH FOR SAME

(75) Inventor: Eduardo M. Rey, Winter Springs, FL (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 111 days.

(21) Appl. No.: 12/996,038

(22) PCT Filed: May 29, 2009

(86) PCT No.: PCT/IB2009/052288
§ 371 (c)(1), (2), (4) Date: Dec. 3, 2010

(87) PCT Pub. No.: WO2009/153682
PCT Pub. Date: Dec. 23, 2009

(65) Prior Publication Data
US 2011/0082359 A1    Apr. 7, 2011

Related U.S. Application Data

(60) Provisional application No. 61/073,383, filed on Jun. 18, 2008.

(51) Int. Cl.
*A61B 5/04* (2006.01)
(52) U.S. Cl.
USPC ............ 600/509; 600/372; 600/382; 600/393
(58) Field of Classification Search
USPC ................. 600/372, 382, 384, 386, 388–393
See application file for complete search history.

(56) References Cited

U.S. PATENT DOCUMENTS

| 4,850,370 | A | 7/1989 | Dower |
| 6,032,063 | A | 2/2000 | Hoar et al. |
| 6,052,614 | A | 4/2000 | Morris, Sr. et al. |
| 6,496,720 | B1 | 12/2002 | Feild |
| 6,721,591 | B2 | 4/2004 | Wei et al. |
| 6,847,836 | B1 | 1/2005 | Sujdak |
| 2001/0025139 | A1 | 9/2001 | Pearlman |
| 2004/0106876 | A1* | 6/2004 | Schmid et al. ............... 600/509 |
| 2004/0176674 | A1 | 9/2004 | Nazeri |
| 2010/0234746 | A1* | 9/2010 | Sebelius .................... 600/509 |

FOREIGN PATENT DOCUMENTS

WO    2006017747 A2    2/2006

* cited by examiner

*Primary Examiner* — Linda Dvorak
*Assistant Examiner* — Brian M Antiskay

(57) ABSTRACT

An electrode patch (40, 40') enables securing five electrodes ($E'$, $A'$, $S'$, $I'$, $N'$) or six electrodes ($V_1'$, $V_6'$, $LA'$, $RA'$, $LL'$, $RL'$) in a predefined pattern. The electrode patch is configured for disposal as a unit on a subject (SUBJ) in a magnetic resonance (MR) scanner (8), and has a maximum electrodes separation ($d_{max}$) of at least 20 centimeters and not more than 50 centimeters. The predefined pattern enables 12-lead electrocardiographic signals to be synthesized from signals acquired by the five or six electrodes in the predefined pattern. A method that can use the electrode patch comprises: acquiring magnetic resonance data with a subject disposed in a MR scanner; securing a plurality of electrodes to the subject in the magnetic resonance scanner, the plurality of electrodes comprising fewer than ten electrodes; and synthesizing twelve leads corresponding to a conventional 12-lead electrocardiograph from electrocardiographic signals acquired by the plurality of electrodes with the subject disposed in the MR scanner.

14 Claims, 2 Drawing Sheets

ELECTROCARDIOGRAPH FOR MAGNETIC RESONANCE IMAGING AND ELECTRODE PATCH FOR SAME

CROSS REFERENCE TO RELATED APPLICATIONS

Figure 1:
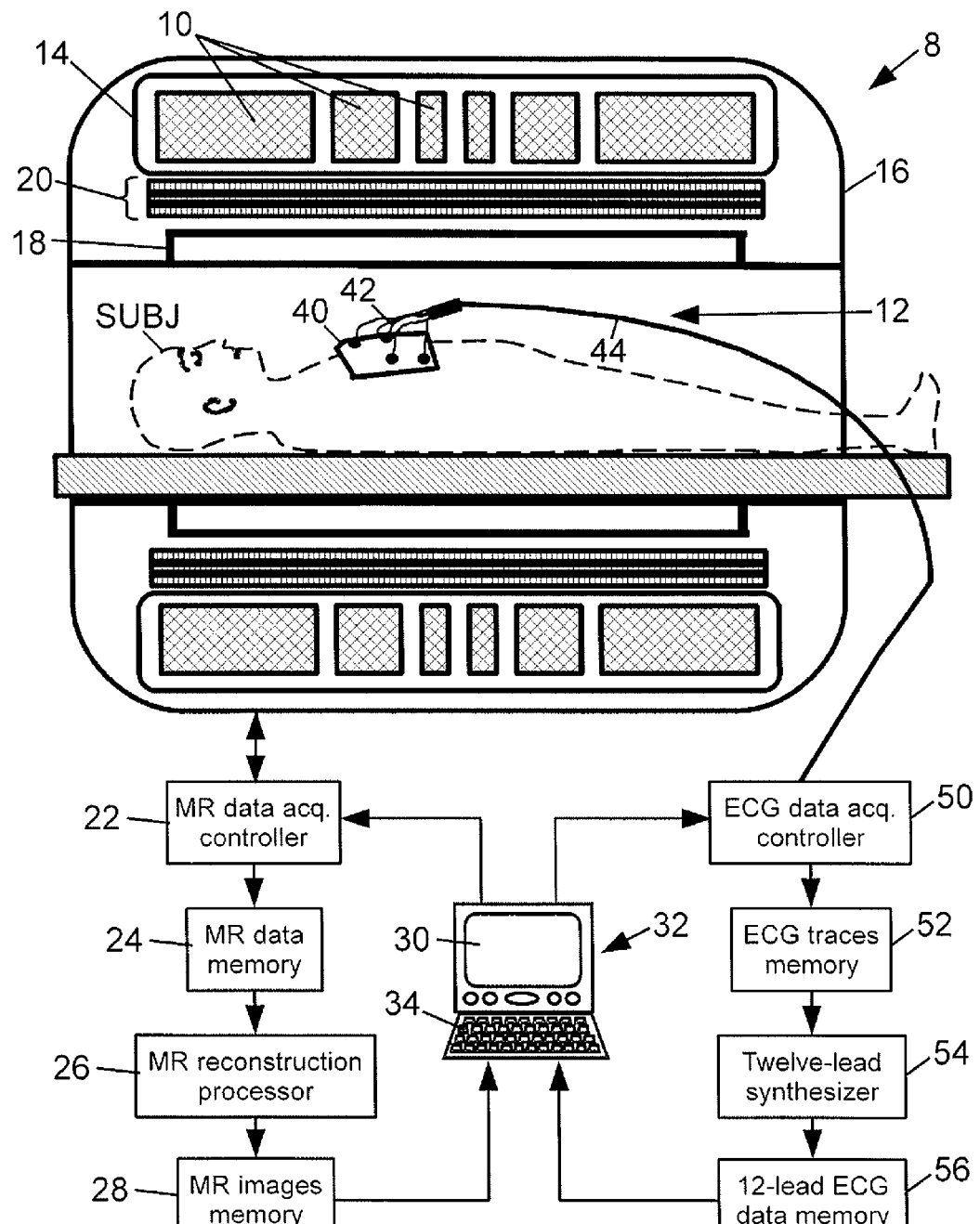

This application claims the benefit of U.S. provisional application Ser. No. 61/073,383 filed Jun. 18, 2008, which is incorporated herein by reference.

The following relates to the medical arts, magnetic resonance arts, electrocardiographic arts, and related arts. It finds application in cardiac gated magnetic resonance imaging and other magnetic resonance applications that are beneficially monitored by electrocardiography, and the like.

Cardiac gated magnetic resonance (MR) imaging entails monitoring the cardiac cycle of a subject during acquisition of MR imaging data. Cardiac gating enables reconstruction of imaging data acquired during a selected portion of the cardiac cycle so as to reduce cardiac motion-related or blood flow-related artifacts. In another cardiac gating application, a cinematic (CINE) sequence of images can be obtained and aligned with the cardiac cycle provided by the cardiac gating. Some other applications of cardiac monitoring during MR imaging include: detecting cardiac arrhythmia or other abnormal episodes so as to exclude imaging data acquired during such episodes; detecting subject distress brought on by claustrophobia or other aspects of the MR imaging experience; and so forth.

Electrocardiography (ECG) is a common technique for monitoring the cardiac cycling. In conventional 12-lead ECG, an electrode is placed on each limb and six electrodes are placed at standard locations on the chest. A complete 12-lead ECG therefore includes ten electrodes placed at ten different standard locations on the subject. Twelve electrical lead signals are acquired using various combinations of these ten electrodes. A skilled cardiologist or other specialist can derive a substantial amount of information about the cardiac activity in three dimensions from 12-lead ECG data.

The 12-lead ECG configuration is standard, and cardiologists are used to interpreting 12-lead ECG data. However, placement of the ten electrodes of a conventional 12-lead ECG is time-consuming and uncomfortable for the subject. An improved lead configuration, known as the EASI lead configuration, enables acquisition of 12-lead ECG data using five or six electrodes, including the conventionally termed "E", "A", "S", and "I" electrodes and one or two additional electrodes. Some known EASI electrode configurations are disclosed, for example, in Dower, U.S. Pat. No. 4,850,370 which is incorporated herein by reference in its entirety, and in Field, U.S. Pat. No. 6,496,720 which is incorporated herein by reference in its entirety.

Heretofore, 12-lead ECG, including EASI and other simplified configurations, has been considered to be incompatible with MR imaging. The electrode wires in a 12-lead ECG are long and frequently cross, giving rise to conductive paths and loops that can conduct large induced electrical currents due to interaction with magnetic fields of the MR imaging. These induced currents can introduce noise into the MR images, the ECG data, or both, and can also present a safety hazard since the large induced electrical currents can lead to heating and subject burns. In addition to these concerns, connecting a subject with a 12-lead ECG would add considerable time and complexity to already-extensive MR imaging sessions.

For monitoring purposes, such as cardiac gating, a 3-lead ECG is typically employed, which has four electrodes arranged close together on the subject's chest, with the maximum separation of any two electrodes being less than about 15 centimeters. The close arrangement of electrodes reduces conductive path lengths and loops. An MR compatible 3-lead ECG system can be constructed using non-magnetic materials for the electrodes and wires. Since only four electrodes are used, connection of the subject to the 3-lead ECG does not unduly lengthen or complicate the MR imaging session.

The reduced number of leads in a 3-lead ECG comes at the cost of reduced information versus a 12-lead ECG. Additionally, cardiologists and other specialists are generally less adept at interpreting 3-lead ECG data as compared with conventional 12-lead ECG data. As a result, the 3-lead ECG is sufficient to provide basic information such as the cardiac cycle period and identification of gross ECG features such as occurrence of the dominant QRS complex. However, the 3-lead ECG is generally inadequate for performing more sophisticated cardiac analysis. This limits the synergistic value of ECG/MR systems.

The following provides a new and improved apparatuses and methods which overcome the above-referenced problems and others.

In accordance with one disclosed aspect, an apparatus comprises: a plurality of electrodes configured to be disposed on a subject in a magnetic resonance scanner, the plurality of electrodes comprising fewer than ten electrodes; and an electrocardiographic instrument operatively connected with the plurality of electrodes and configured to synthesize twelve leads corresponding to a conventional 12-lead electrocardiographic instrument from electrocardiographic signals acquired from the plurality of electrodes. In some embodiments the apparatus further comprises said magnetic resonance scanner configured to acquire magnetic resonance data of a subject disposed in the magnetic resonance scanner.

In accordance with another disclosed aspect, an electrode patch is disclosed for securing a plurality of electrodes consisting of five or six electrodes in a predefined pattern. The electrode patch is configured for disposal as a unit on a subject in a magnetic resonance scanner. The predefined pattern has a maximum electrodes separation of at least 20 centimeters and not more than 50 centimeters. The predefined pattern enables 12-lead electrocardiographic signals to be synthesized from signals acquires by the five or six electrodes in the predefined pattern.

In accordance with another disclosed aspect, a method comprises: acquiring magnetic resonance data with a subject disposed in a magnetic resonance scanner; securing a plurality of electrodes to the subject in the magnetic resonance scanner, the plurality of electrodes comprising fewer than ten electrodes; and synthesizing twelve leads corresponding to a conventional 12 lead electrocardiograph from electrocardiographic signals acquired by the plurality of electrodes with the subject disposed in the magnetic resonance scanner.

One advantage resides in acquiring conventional 12-lead ECG data in an MR environment without introducing problematic electrically conductive paths or loops.

Another advantage resides in facilitating the MR operator in mounting an effective number of electrodes for acquiring 12-lead ECG data without introducing a substantial increase in MR workflow complexity or time.

Further advantages of the present invention will be appreciated to those of ordinary skill in the art upon reading and understand the following detailed description.

FIG. 1 diagrammatically shows a combined magnetic resonance/electrocardiographic data acquisition system.

Figure 2:
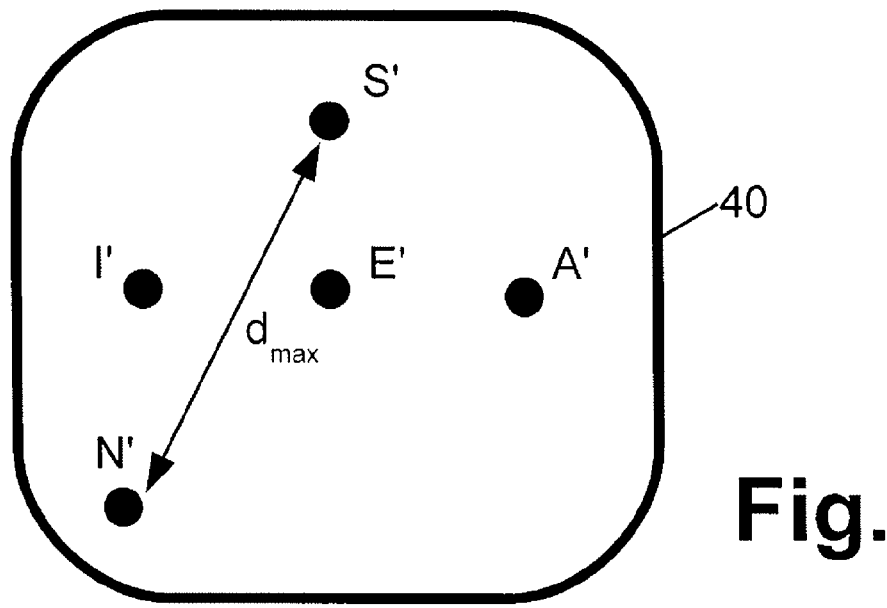

FIG. 2 diagrammatically shows an electrode patch for use in the system of FIG. 1 providing a predefined configuration for five electrodes capable of providing synthesized 12-lead electrocardiographic data.

Figure 3:
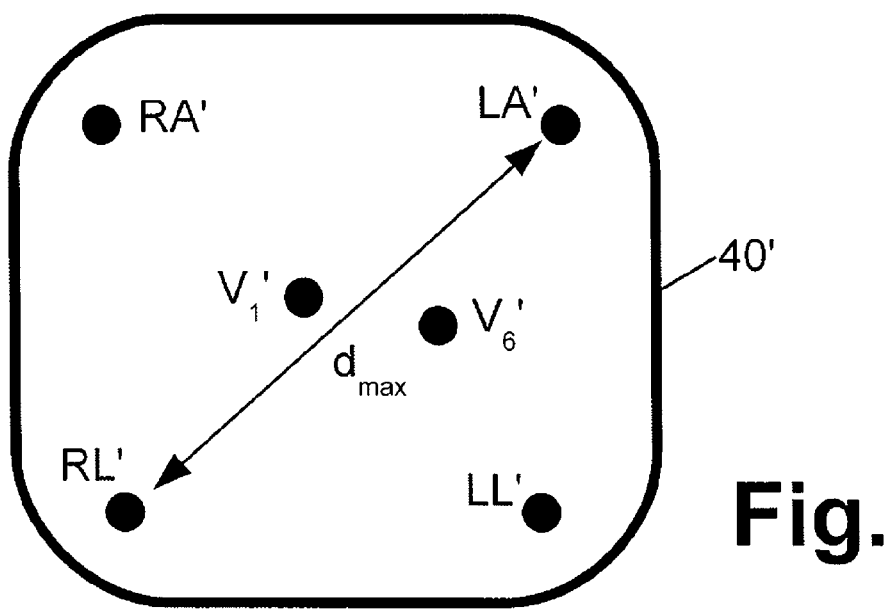

FIG. 3 diagrammatically shows an electrode patch for use in the system of FIG. 1 providing a predefined configuration for six electrodes capable of providing synthesized 12-lead electrocardiographic data.

With reference to FIG. 1, a cardiac diagnostic or monitoring system includes a magnetic resonance (MR) scanner 8 having a main magnet 10 that generates a static main ($B_0$) magnetic field in an examination region 12. In the illustrated embodiment, the main magnet 10 is a superconducting magnet disposed in a cryogenic vessel 14 employing helium or another cyrogenic fluid; alternatively a resistive main magnet can be used. In the illustrated embodiment, the magnet assembly 10, 14 is disposed in a generally cylindrical scanner housing 16 defining the examination region 12 as a cylindrical bore; alternatively, other geometries such as an open MR geometry can also be used. Magnetic resonance is excited and detected by one or more radio frequency coils, such as an illustrated whole-body quadrature body coil 18 or one or more local coils or coil arrays such as a head coil or chest coil. The excited magnetic resonance is spatially encoded, phase- and/or frequency-shifted, or otherwise manipulated by magnetic field gradients selectively generated by a set of magnetic field gradient coils 20.

The magnetic resonance scanner 8 is operated by a magnetic resonance data acquisition controller 22, suitably embodied by a dedicated digital processing device, a suitably programmed general purpose computer, or so forth, to generate, spatially encode, and read out magnetic resonance data, such as projections or k-space samples, that are stored in a magnetic resonance data memory 24. The acquired spatially encoded magnetic resonance data are reconstructed by a magnetic resonance reconstruction processor 26 to generate one or more images of a subject SUBJ disposed in the examination region 12. The reconstruction processor 26 employs a reconstruction algorithm comporting with the spatial encoding, such as a backprojection-based algorithm for reconstructing acquired projection data, or a Fourier transform-based algorithm for reconstructing k-space samples. The one or more reconstructed images are stored in a magnetic resonance images memory 28, and are suitably displayed on a display 30 of a user interface 32, or printed using a printer or other marking engine, or transmitted via the Internet or a digital hospital network, or stored on a magnetic disk or other archival storage, or otherwise utilized. The illustrated user interface 32 also includes one or more user input devices such as an illustrated keyboard 34, or a mouse or other pointing-type input device, or so forth, which enables a radiologist, cardiologist, or other user to manipulate images and, in the illustrated embodiment, interface with the magnetic resonance scanner controller 22.

With continuing reference to FIG. 1, the cardiac diagnostic or monitoring system further includes an electrocardiograph (ECG) including a set of electrodes mounted via an electrode patch 40 to a chest or torso of the subject SUBJ. The electrode patch 40 including the electrodes is constructed of materials having low magnetic susceptibility and/or includes small-sized components (such as electrodes) of higher magnetic susceptibility, so as to not interfere with, or minimally interfere with, the magnetic resonance data acquisition. Such interference is further mitigated or eliminated by the use of a short pigtail of wires 42 to electrically connect the electrodes of the electrode patch 40 with a cable bundle 44. The electrode patch 40 includes fewer than ten electrodes, and preferably includes five or six electrodes. The short wires of the short pigtail of wires 42 and the reduced number of electrodes (as compared with a conventional 12-lead ECG configuration) ensures that the corresponding electrically conductive loops are small, and reduces or eliminates crossed wires. The cable bundle 44 is shielded by an electrically conductive sheath, such as surrounding wire mesh or metal fiber-embedded sheathing, to further reduce interaction with fields generated by the magnetic resonance scanner 8.

The cable bundle 44 conveys electrical signals from the electrodes of the electrode patch 40 to an ECG data acquisition controller 50 that acquires electrical traces from the electrodes and stores the acquired traces in an ECG traces memory 52. Because the electrode patch 40 includes fewer than ten electrodes, a conventional 12-lead ECG output cannot be directly generated. However, a selected configuration of fewer than ten electrodes defined by the electrode patch 40, a 12-lead synthesizer suitably processes the ECG traces to synthesize a conventional 12-lead output that is stored in a 12-lead ECG data memory 56, and is combined with the MR images or imaging process to generate synergistic information.

For example, the 12-lead output can be used to perform precise ECG gating in which the cardiac phase is estimated from known features of the conventional 12-lead ECG signal. In contrast, ECG gating employing a 3-lead ECG is more limited in its ability to identify cardiac phase. In the illustrated embodiment, the 12-lead ECG data is input to the user interface 32 where cardiac gating signals are generated. The cardiac gating signals can be generated using an automated algorithm that detects 12-lead ECG features corresponding to particular cardiac phases. Additionally or alternatively, the cardiac gating signals can be generated in a semi-manual mode, by having a skilled cardiologist review the 12-lead ECG traces and manually identify features indicative of selected cardiac phases. In some embodiments, the 12-lead ECG traces are input directly to the MR scanner controller 22, rather than using the user interface 32 as an intermediary interface.

As another example of attainable synergistic information, the synthesized 12-lead ECG signal can be utilized together with simultaneously acquired MR images in a diagnostic fashion. By having the user interface 32 display MR images together with corresponding simultaneously acquired synthesized 12-lead ECG traces, a skilled cardiologist can correlate cardiac events observed in the synthesized 12-lead ECG traces with cardiac activity imaged by MR. For example, the 12-lead ECG data may indicate a cardiac ischemia that is adversely affecting the pumping behavior of the heart. By correlating the ischemic 12-lead ECG feature with simultaneously acquired MR images, the skilled cardiologist may more readily identify the precise spatial location and extent of the cardiac ischemia in the MR images.

With continuing reference to FIG. 1 and with further reference to FIG. 2, an illustrative embodiment of the electrode patch 40 includes five electrodes. These electrodes are laid out in a modified EASI pattern, including modified electrodes E', A', S', and I' of the EASI configuration and a modified neutral or ground electrode N'. The electrodes are modified respective to the EASI pattern in that they are closer together, having a maximum electrodes separation $d_{max}$ of no more than 50 centimeters, and preferably no more than 45 centimeters. That is, no two electrodes of the plurality of electrodes in the predefined pattern defined by the electrode patch 40 are separated by more than 50 centimeters, and more preferably by no more than 45 centimeters. On the other hand, in order to provide sufficient lead distance, the maximum electrodes separation $d_{max}$ is preferably at least 20 centimeters, and is more preferably at least 30 centimeters.

The electrode patch 40 implements a modified EASI configuration in which the spacing of electrodes is modified while the general placement configuration is retained. Accordingly, the twelve-lead synthesizer 54 or other electrocardiographic instrument is suitably configured to synthesize the twelve leads using EASI linear transforms, such as are disclosed in Dower, U.S. Pat. No. 4,850,370 which is incorporated herein by reference in its entirety, or as described in Feild, U.S. Pat. No. 6,496,720 which is incorporated herein by reference in its entirety.

With reference to FIG. 3, the electrode patch can be configured to provide other configurations or layouts of fewer than ten electrodes, where the electrodes configuration is selected to enable the synthesizing a standard 12-lead ECG. An illustrative electrode patch 40' diagrammatically shown in FIG. 3 and suitably substituted for the electrode patch 40 in FIG. 1 includes six electrodes, namely: a modified $V_1$ electrode $V_1'$; a modified $V_6$ electrode $V_6'$; a modified "left arm" electrode LA'; a modified "right arm" electrode RA'; a modified "left leg" electrode LL'; and a modified "right leg" electrode RL'. The modified electrodes $V_1'$, $V_6'$ correspond precisely or approximately to the $V_1$, $V_6$ electrodes of a conventional 12-lead ECG electrode configuration, while the modified electrodes LA', RA', LL', RL' correspond to the limb electrodes of a conventional 12-lead ECG electrode configuration, but modified in that the modified electrodes LA', RA', LL', RL' are disposed on the chest or torso rather than on the limbs, so as to produce a more compact arrangement. The outputs of the six-electrode configuration of the electrode patch 40' can be input to the twelve-lead synthesizer 54 or other electrocardiographic instrument suitably configured to synthesize the twelve leads using transforms appropriate for the six-electrode configuration of electrode patch 40'. For example, suitable transforms are disclosed in Wei et al., U.S. Pat. No. 6,721,591 which is incorporated herein by reference in its entirety.

In both electrode patches 40, 40' the modified electrodes configuration has sufficient breadth (e.g., at least 20 centimeters maximum electrodes separation in some embodiments, or at least 30 centimeters maximum electrodes separation in other embodiments) so that the synthesized 12-lead ECG signals provide a good approximation of a physical (ten electrode) 12-lead ECG system. At the same time, in both electrode patches 40, 40' the modified electrodes configuration has sufficiently limited breadth (e.g., no more than 50 centimeters maximum electrodes separation in some embodiments, or no more than 45 centimeters maximum electrodes separation in other embodiments) so that the size of conductive loops and their likelihood of crossing is minimized, thus making MR-compatible the ECG system of FIG. 1 including the electrode patch 40 (or, alternatively, the electrode patch 40') and the short pigtail of wires 42 and cable bundle 44. It will be appreciated that the constraint on the maximum electrodes separation enables the short pigtail of wires 42 to have correspondingly short wires.

The electrodes configuration defined by the electrode patch 40, that is, the positions of the electrodes E', A', S', I', N', or alternatively the electrodes configuration defined by the electrode patch 40', that is, the positions of the electrodes $V_1'$, $V_6'$, LA', RA', LL', RL', are suitably determined by performing body mapping constrained by a maximum electrodes separation constraint, the plurality of electrodes being secured to the subject in the magnetic resonance scanner in the determined electrodes pattern. The maximum electrodes separation constraint may be, for example, to have a maximum electrodes separation $d_{max}$ of no more than 50 centimeters; or, to have a maximum electrodes separation $d_{max}$ of no more than 45 centimeters; or so forth. Optionally, the performed body mapping is further constrained by a minimum value constraint for the maximum electrodes separation, for example requiring the maximum electrodes separation to be at least 20 centimeters, or at lest 30 centimeters, or so forth. It is to be appreciated that one or more of the electrodes may be in the same place as in the "standard" configuration. For example, the electrode patch 40 may have the electrode E' located at the same position as in a conventional EASI configuration; however, the electrode E' is still modified in that its position relative to the other electrodes A', S', I', N' is modified respective to the conventional EASI configuration.

The illustrative electrode patches 40, 40' are examples. Other configurations of fewer than 10 electrodes are also contemplated, so long as the configuration is selected such that the conventional 12-lead ECG signals can be synthesized. Typically, five or six electrodes are preferable, as this provides enough data for accurate synthesization of the 12-lead ECG while keeping the number of electrodes low to enhance MR compatibility. In some embodiments, it is contemplated to have differently sized electrode patches for differently sized subjects. For example, there may be a differently sized electrode patches for neonatal, pediatric, and adult subjects. The electrode patches 40, 40' are optionally consumable items that are replaced for each subject. The physical connection of the electrodes and the wires of the pigtail 42 can be made by snap-connectors or the like to facilitate rapid connection and disconnection. The use of the electrode patches 40, 40' facilitate rapid deployment of the ECG in the MR system, for example just before commencing an MR imaging session. However, it is also contemplated to perform the disclosed MR/ECG methods including simulation of 12-lead ECG data by using electrodes that are applied separately and without the use of a pattern-defining electrode patch.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An apparatus comprising:
   a magnetic resonance scanner configured to acquire magnetic resonance data of a subject disposed in the magnetic resonance scanner;
   a plurality of electrodes are adapted to be disposed on the subject in the magnetic resonance scanner, the plurality of electrodes consisting of five electrodes or six electrodes;
   a cable bundle connected with the plurality of electrodes to convey electrical signals from the plurality of electrodes, the cable bundle being shielded by an electrically conductive sheath comprising surrounding wire mesh or metal fiber-embedded sheathing; and
   an electrocardiographic instrument connected with the plurality of electrodes by the cable bundle and configured to synthesize twelve leads corresponding to a conventional 12-lead electrocardiographic instrument from electrocardiographic signals acquired from the plurality of electrodes.

2. The apparatus as set forth in claim 1, further comprising:
an electrode patch securing the plurality of electrodes in a predefined pattern, the electrode patch being configured for disposal as a unit on the subject in the magnetic resonance scanner.

3. The apparatus as set forth in claim 2, wherein no two electrodes of the plurality of electrodes in the predefined pattern are separated by more than 50 centimeters.

4. The apparatus as set forth in claim 3, wherein no two electrodes of the plurality of electrodes in the predefined pattern are separated by more than 45 centimeters.

5. The apparatus as set forth in claim 2, wherein the predefined pattern comprises a modified EASI electrode pattern that is modified respective to the EASI electrode pattern in having a reduced maximum electrodes separation.

6. The apparatus as set forth in claim 5, wherein the electrocardiographic instrument is configured to synthesize the twelve leads using EASI linear transforms.

7. An apparatus comprising:
an electrode patch securing a plurality of electrodes consisting of five or six electrodes in a predefined pattern, the electrode patch being configured for disposal as a unit on a subject; and
a cable bundle connected with the electrodes of the electrode patch to convey electrical signals from the electrodes of the electrode patch, the cable bundle being shielded by an electrically conductive sheath comprising surrounding wire mesh or metal fiber-embedded sheathing;
wherein the electrode patch is configured for disposal as a unit on a subject in a magnetic resonance scanner at least by the connected cable bundle being sheathed by said electrically conductive sheath comprising surrounding wire mesh or metal fiber-embedded sheathing; and,
wherein the predefined pattern has a maximum electrodes separation of at least 20 centimeters and not more than 50 centimeters, the predefined pattern enabling 12-lead electrocardiographic signals to be synthesized from signals acquired by the five or six electrodes in the predefined pattern.

8. The apparatus of claim 7, wherein the predefined pattern is a modified EASI electrode pattern that is modified respective to the EASI electrode pattern in that the maximum electrodes separation is at least 20 centimeters and not more than 50 centimeters.

9. A method comprising:
acquiring magnetic resonance data with a subject disposed in a magnetic resonance scanner;
securing a plurality of electrodes to the subject in the magnetic resonance scanner, the plurality of electrodes comprising fewer than ten electrodes;
acquiring electrocardiographic signals using the plurality of electrodes with the subject disposed in the magnetic resonance scanner; and
synthesizing twelve leads corresponding to a conventional 12-lead electrocardiograph from the electrocardiographic signals acquired using the plurality of electrodes with the subject disposed in the magnetic resonance scanner.

10. The method as set forth in claim 9, wherein the securing comprises:
securing the electrodes of the plurality of electrodes with no two secured electrodes separated by more than 45 centimeters.

11. The method as set forth in any claim 9, wherein the securing comprises:
securing the electrodes in a modified EASI electrode pattern that is modified respective to the EASI electrode pattern in having a reduced maximum electrodes separation.

12. The method as set forth in claim 9, wherein the plurality of electrodes consists of five electrodes or six electrodes.

13. The method as set forth in claim 9, further comprising:
determining an electrodes pattern by performing body mapping constrained by a maximum electrodes separation constraint, the plurality of electrodes being secured to the subject in the magnetic resonance scanner in the determined electrodes pattern.

14. The method as set forth in claim 9, wherein the acquiring of electrocardiographic signals comprises:
conveying the electrocardiographic signals via a cable bundle; and
shielding the cable bundle by electrically conductive wire mesh or metal fiber-embedded sheathing.

* * * * *